US006951902B2

(12) United States Patent
McDonald et al.

(10) Patent No.: US 6,951,902 B2
(45) Date of Patent: Oct. 4, 2005

(54) TWO DIMENSIONAL POLYMER THAT GENERATES NITRIC OXIDE

(75) Inventors: William F. McDonald, Utica, OH (US); Amy B. Koren, Lansing, MI (US)

(73) Assignee: Michigan Biotechnology Institute, Lansing, MI (US)

( * ) Notice: Subject to any disclaimer, the term of this patent is extended or adjusted under 35 U.S.C. 154(b) by 0 days.

(21) Appl. No.: 10/222,370

(22) Filed: Aug. 16, 2002

(65) Prior Publication Data

US 2004/0033242 A1 Feb. 19, 2004

(51) Int. Cl.$^7$ .......................... C08L 77/00; C08G 69/10

(52) U.S. Cl. ...................... 525/54.3; 525/420; 525/421; 525/423; 525/424; 525/427; 525/431

(58) Field of Search ................................ 525/54.3, 420, 525/421, 423, 424, 427, 431

(56) References Cited

U.S. PATENT DOCUMENTS

| | | | |
|---|---|---|---|
| 3,695,921 A | 10/1972 | Shepherd et al. | |
| 4,054,139 A | 10/1977 | Crossley | |
| 4,128,633 A | 12/1978 | Lorenz et al. | |
| 4,217,338 A | 8/1980 | Quash | |
| 4,302,368 A | 11/1981 | Dudley et al. | |
| 4,310,509 A | 1/1982 | Berglund et al. | |
| 4,323,557 A | 4/1982 | Rosso et al. | |
| 4,357,476 A | 11/1982 | Reinchr et al. | |
| 4,419,444 A | 12/1983 | Quash | |
| 4,442,133 A | 4/1984 | Greco et al. | |
| 4,581,028 A | 4/1986 | Fox, Jr. et al. | |
| 4,603,152 A | 7/1986 | Laurin et al. | |
| 4,605,564 A | 8/1986 | Kulla et al. | |
| 4,642,104 A | 2/1987 | Sakamoto et al. | |
| 4,675,347 A | 6/1987 | Mochizuki et al. | |
| 4,678,660 A | 7/1987 | McGary et al. | |
| 4,720,512 A | 1/1988 | Hu et al. | |
| 4,786,556 A | 11/1988 | Hu et al. | |
| 4,865,870 A | 9/1989 | Hu et al. | |
| 4,933,178 A | 6/1990 | Capelli | |
| 4,954,526 A | 9/1990 | Keefer | |
| 4,987,181 A | 1/1991 | Bichon et al. | |

(Continued)

FOREIGN PATENT DOCUMENTS

| | | |
|---|---|---|
| EP | 0 882 461 | 12/1998 |
| EP | 0 969 056 | 1/2000 |
| GB | 2 084 466 | 4/1982 |
| GB | 2 153 235 | 8/1985 |
| GB | 2 225 580 | 6/1990 |
| JP | 11 222 402 | 8/1999 |
| WO | WO 86/02561 | 5/1986 |
| WO | WO 94/13870 | 6/1994 |
| WO | WO 95/05400 | 2/1995 |
| WO | WO 01/11956 | 2/2001 |

OTHER PUBLICATIONS

Saaveda et al., "The Secondary Amine/Nitric Oxide Complex Ion as Nucleophile and Leaving Group in SnAr Reactions", J. Org. Chem, 2001, 66, 3090–3098, Apr. 11, 2001.
Zavorin et al., "Nitrate Esters as Nitric Oxide Donors: SS–Nitrates", Organic Letters, 3, 8, 1113–1116, Mar. 20, 2001.
Espadas–Torre et al., "Thromboresistant Chemical Sensors Using Combined Nitric Oxide Release/Ion Sensing Polymeric Films", J. Am. Chem. Soc., 119; 2321–22, 1997.
Schoenfisch et al.,"Improving the Thromboresistivity of Chemical Sensors via Nitric Oxide Release . . . ", Anal. Chem., 72, 1119–1126, Mar. 15, 2000.
Barker et al., "Cellular Applications of a Sensitive and Selective Fiber Optic Nitric Oxide Biosensor . . . ", Anal. Chem., 71; 2071–2075, Jun. 1, 1999.
Satoh et al., "Immobilization of Saccharides and Peptides on 96–Well Microtiter Plates with Methyl Vinyl ether–Maleic Anhydride Copolymer", Anal. Biochem., 260, 96–102, 1998.
Vercruysse et al., "Synthesis and in Vitro Degradation of New Polyvalent Hydrazide Cross–Linked Hydrogels of Hyaluronic Acid", Bioconj. Chem., 8, 686–694, 1997.
O'Shannessy et al., Immobilization of Glycoconjugates by Their Oligosaccharides: Use of Hydrazido–Derivatized Matrices, Anal. Biochem., 191, 1–8, 1990.
Ito et al., Preparation of High Capacity Affinity Adsorbents Using New Hydrazino–Carriers and Their Use for Low and High Performance Affinity Cheomatography of Lectins, J. Biochem. (Tokyo), 99, 1267–1272.
Junowicz et al., The Derivatization of Oxidized Polysaccharides for Protein Immobilization and Affinity Chromatography Biochim. Biophys. Acta 428, 157–165, 1976.
Miron et al., Polyacrylhyrdazio–Agarose: Preparation via Periodate Oxidation and use for Enzyme Immobilization and Affinity Chromatography, J. Chromatogr., 215, 55–63, 1981.

(Continued)

*Primary Examiner*—Ana Woodward
(74) *Attorney, Agent, or Firm*—Foley & Lardner LLP

(57) ABSTRACT

A polymeric composition that generates nitric oxide and a process for rendering the surface of a substrate nonthrombogenic by applying a coating of the polymeric composition to the substrate are disclosed. The composition comprises: (1) a crosslinked chemical combination of (i) a polymer having amino group-containing side chains along a backbone forming the polymer, and (ii) a crosslinking agent containing functional groups capable of reacting with the amino groups; and (2) a plurality of nitric oxide generating functional groups associated with the crosslinked chemical combination. Once exposed to a physiological environment, the coating generates nitric oxide thereby inhibiting platelet aggregation. In one embodiment, the nitric oxide generating functional groups are provided by a nitrated compound (e.g., nitrocellulose) imbedded in the polymeric composition. In another embodiment, the nitric oxide generating functional groups comprise $N_2O_2^-$ groups covalently bonded to amino groups on the polymer.

40 Claims, 6 Drawing Sheets

U.S. PATENT DOCUMENTS

| | | | |
|---|---|---|---|
| 4,999,210 | A | 3/1991 | Solomon et al. |
| 5,019,096 | A | 5/1991 | Fox, Jr. et al. |
| 5,039,705 | A | 8/1991 | Keefer et al. |
| 5,069,907 | A | 12/1991 | Mixon et al. |
| 5,155,137 | A | 10/1992 | Keefer et al. |
| 5,185,376 | A | 2/1993 | Diodati et al. |
| 5,316,912 | A | 5/1994 | Heimgartner et al. |
| 5,328,698 | A | 7/1994 | Onwumere et al. |
| 5,344,411 | A | 9/1994 | Domb et al. |
| 5,405,919 | A | 4/1995 | Keefer et al. |
| 5,482,925 | A | 1/1996 | Hutsell |
| 5,641,855 | A | 6/1997 | Scherr et al. |
| 5,650,447 | A | 7/1997 | Keefer et al. |
| 5,691,423 | A | 11/1997 | Smith et al. |
| 5,709,672 | A | 1/1998 | Illner |
| 5,762,638 | A | 6/1998 | Shikani et al. |
| 5,814,656 | A | 9/1998 | Saavedra et al. |
| 5,962,520 | A | 10/1999 | Smith et al. |
| 5,994,444 | A | 11/1999 | Trescony et al. |
| 6,030,632 | A | 2/2000 | Sawan et al. |
| 6,042,877 | A | 3/2000 | Lyon et al. |
| 6,056,967 | A | 5/2000 | Steuerle et al. |
| 6,087,462 | A | 7/2000 | Bowers et al. |
| 6,121,027 | A | 9/2000 | Clapper et al. |
| 6,153,724 | A | 11/2000 | Hollingsworth |
| 6,162,487 | A | 12/2000 | Darouiche |
| 6,200,558 | B1 | 3/2001 | Saavedra et al. |
| 6,224,579 | B1 | 5/2001 | Modak et al. |
| 6,232,336 | B1 | 5/2001 | Hrabie et al. |
| 6,232,434 | B1 | 5/2001 | Stamler et al. |
| 6,270,779 | B1 | 8/2001 | Fitzhugh et al. |
| 6,319,674 | B1 | 11/2001 | Fulcrand et al. |
| 6,340,465 | B1 | 1/2002 | Hsu et al. |
| 6,399,714 | B1 | 6/2002 | Huang et al. |
| 6,495,657 | B1 * | 12/2002 | McDonald et al. ......... 528/310 |
| 6,509,104 | B2 | 1/2003 | Huang et al. |
| 2003/0077243 | A1 * | 4/2003 | Fitzhugh et al. |

OTHER PUBLICATIONS

Heimgartner, et al., Polyacrylic Polyhydrazides as Reagents for Detection of Glycoproteins, Anal. Biochem., 181, 182–189, 1989.

Fleminger et al., Oriented Immobilization of Peridate–Oxidized Monoclonal Antibodies on Amino and Hydrazide Derivatives of Eupergit C, Applied Biochem., 23, 123–137, 1990.

Del Rosso et al., Binding of the Basement–Membrane Glycoprotein Lamnin to Glycosaminoglycans, Biochem. J., 199, 699–704, 1981.

Henderson et al., Immobilised Phosphines Incorporation the Chiral Bioploymers Chitosan and Chitin, J. Chem. Soc., Chem. Commun., 9, 1863–1864, 1994.

Petach et al., A New Coupling Reagnet for the Covalent Immobilisation of Enzymes, J. Chem. Soc., Chem. Commun., 17, 2181–2182, 1994.

Cochrane et al., Application of Tris(hydroxymethyl) Phophine as a Coupling Agent for Alcohol Dehydrogenase Immobilization, Enzyme Microbial Technol., 18, 373–378, 1996.

Inman et al., Synthesis of Large Haptenic Compounds Having a Covalent Functional Group That Permits Convalent Linkage to Proteins, Cell Surfaces, Immunochemistry, 10, 153–163, 1973.

Ellis et al., Water–Soluble Tris(hydroxymethyl) Phospine Complexes with Nickel, Palladium, and Platinum, Inorg. Chem., 31, 3026–3033, 1992.

Lin et al., Preparation of Surface–modified Albumin Nanospheres, Biomaterials, V. 18, N. 7, 559–565, 1997.

Marconi et al., New Polyurethane Compsitions able to bond high Amounts of both Albumin and Heparin, V. 16, N. 6, 449–456, 1995.

Oswald et al., "Properties of a Thermostable B–Glycosides Immobilized Using Tris(hydroxymethyl) Phosphine as a Highly Effective Coupling Agent", Enzyme Microbial Technol., 23, 14–19, 1998.

Isosaki et al., Immobilization of Protein Ligands with Methyl Vinyl Ether–maleic Anhydride Copolymer, J. Chromatogr., 597, 123–128, 1992.

Patent Abstracts of Japan vol. 1999, No. 13, Nov. 30, 1999 & JP 11 222402 A (Osaka Gas Co. Ltd), Aug. 17, 1999 abstract.

* cited by examiner

200
TWO DIMENSIONAL POLYMER THAT GENERATES NITRIC OXIDE

STATEMENT REGARDING FEDERALLY SPONSORED RESEARCH OR DEVELOPMENT

This Invention was made with Government support under NREL Subcontract NO. XXE-9-29058-01, Prime Contract No. DE-AC36-98GO10337 awarded by the Department of Energy. The Government has certain rights in this invention.

BACKGROUND OF THE INVENTION

1. Field of the Invention

This invention relates to a polymeric composition that generates nitric oxide, and more particularly to a two dimensional polymer having nitric oxide generating functional groups or compounds including nitric oxide generating functional groups bound to the polymer for generating nitric oxide.

2. Description of the Related Art

It is well known that when blood comes into contact with a surface other than the natural wall of a blood vessel, the activation of certain circulating substances results in the coagulation of the blood. If thrombi are formed on portions of the surface which contact blood flow, there is a risk that the thrombi will be released and cause serious blood circulation disturbances called thrombosis. As a result, extensive investigations have been undertaken over many years to find materials having a reduced tendency to form thrombosis. This area of research has become increasingly important with the development of various objects and articles which can be in contact with blood, such as artificial organs, vascular grafts, probes, cannulas, catheters and the like.

Synthetic polymeric materials have come to the fore as preferred materials for such articles. However, these polymeric materials have the major drawback of being thrombogenic. Accordingly, numerous procedures for rendering a polymeric surface non-thrombogenic have been proposed. (As used herein, "non-thrombogenic" and "antithrombogenic" refer to any material which inhibits thrombus formation on a surface.) One known approach for counteracting thrombogenicity of a polymeric surface has been the use of polymer treatments or polymer coatings that serve to inhibit platelet aggregation on the polymeric surface. For instance, functional groups or compounds that inhibit platelet aggregation may be bound to or imbedded in a polymer matrix, or bound to or imbedded in a polymer coating that is applied to the polymer matrix. Typically, antithrombogenic polymer coatings can also be applied to other materials such as metals and ceramics.

For example, U.S. Pat. No. 5,994,444 reports that nitric oxide inhibits platelet activation and discloses a polymeric material capable of releasing nitric oxide so as to inhibit platelet activation. The polymeric material is stated to be useful for lining blood-contacting surfaces of implantable or extracorporeal medical devices so as to reduce or eliminate the undesired effects of platelet aggregation or thrombogenesis. In a preferred embodiment, the polymeric material is capable of generating, donating or releasing nitric oxide in situ, preferably by producing nitric oxide as a result of a chemical conversion of a nitric oxide donor upon hydration of the polymer matrix. In a particularly preferred embodiment, the polymeric material comprises a biodegradable polymer, such as polylactic acid, that yields at least one degradative product, such as lactic acid, that facilitates the conversion of an acid-labile nitric oxide donor, such as inorganic nitrite, to nitric oxide by serving as either an acid or a reducing agent, or both.

U.S. Pat. No. 5,185,376 also reports that compounds including nucleophile-nitric oxide complexes which possess at least one $N_2O_2^-$ functional group decompose in vivo to release nitric oxide and thereby inhibit platelet aggregation. U.S. Pat. Nos. 5,691,423 and 5,405,919 disclose polymeric compositions including a polymer and these nitric oxide generating $N_2O_2^-$ functional groups.

While these nitric oxide releasing polymers may serve to inhibit platelet aggregation on a surface, the preparation of these polymers can present problems. For instance, the preparation of these polymers often requires the coupling of a nitric oxide releasing functional group to a functional group on the polymer. Typically, these coupling reactions are inefficient for various reasons. One method for increasing the efficiency of these coupling reactions involves synthesizing a polymer having side chains with the necessary functional groups. However, the introduction of side chains on a polymer backbone presents further difficulties. One strategy for introducing side chains to a main chain of a polymer is to add the side chains to the preformed main chain. However, this is generally not satisfactory because of the lack of predictability and reproducibility of stoichiometry, under-derivitization for stearic reasons, difficulty in accessing the interior of the polymer, poor solubility of the polymer, and inefficient coupling reactions. An alternative method for introducing side chains to a main chain of a polymer is to attach the desired side chain to each monomer prior to polymer chain formation. This method is generally more efficient but the subsequent coupling of the monomers often requires activating groups to be attached to one or both coupling sites.

These nitric oxide releasing polymers may also exhibit less than ideal physical properties. For example, the nitric oxide releasing polymer is fairly hard and brittle as a result of the ion formation upon addition of the nitric oxide forming the nitric oxide releasing group (Keefer has defined the nitric oxide releasing groups as diazeniumdiolates). Upon forming a film, the nitric oxide releasing polymer forms a "powdery" surface that is easily removed. Also, the film is easily damaged. Therefore, the coating requires some modification in order to form a proper coating that stays in place upon immersion in an aqueous environment.

Thus, there is a need for an antithrombogenic polymer having nitric oxide generating functional groups and having improved physical properties such that the polymer may reliably adhere to substrate surfaces. Furthermore, there is a need for a process that efficiently prepares a polymer having side chains with a functional group that readily bonds to a nitric oxide generating functional group such that an antithrombogenic polymer may be prepared from the polymer and a compound having a nitric oxide generating functional groups.

SUMMARY OF THE INVENTION

The foregoing needs are met by a polymeric composition capable of generating nitric oxide, wherein the polymeric composition comprises (1) a crosslinked chemical combination of (i) a polymer having side chains along a backbone forming the polymer, at least two of the side chains containing an amino group, and (ii) a crosslinking agent containing at least two functional groups capable of reacting with the amino groups; and (2) a plurality of nitric oxide generating functional groups associated with the crosslinked chemical combination. An article according to the invention comprises a substrate and a coating of the polymeric composition disposed, on at least a, portion of the substrate.

A composition according to the invention generates nitric oxide by way of nitric oxide generating functional groups associated with the crosslinked chemical combination (i.e., the crosslinked polymer). As used herein, a nitric oxide generating functional group is "associated" with the crosslinked polymer if the nitric oxide generating functional group is directly or indirectly, physically or chemically bound to the crosslinked polymer. A nitric oxide generating functional group may be physically bound to the crosslinked polymer by entrapping, imbedding or otherwise containing a compound having a nitric oxide generating functional group within the crosslinked polymer network structure. For example, coprecipitation techniques may be used to achieve physical association. A nitric oxide generating functional group may be chemically bound to the crosslinked polymer by way of a chemical reaction wherein a nitric oxide generating functional group is covalently or ionically bonded to the crosslinked polymer. The nitric oxide generating functional group may be chemically bonded to any portion of the network structure of the crosslinked polymer such as the polymer backbone or pendant groups on the polymer backbone. Thus, various techniques for associating nitric oxide generating functional groups in or on the crosslinked polymer of the polymeric composition are contemplated herein.

The polymer used in the polymeric composition comprises a polymer having side chains along a backbone forming the polymer wherein at least two of the side chains contain an amino group (—NRH, —NH$_2$, —NRH$_2^+$, —NH$_3^+$). In one example embodiment, the polymer is a polyamide having amino substituted alkyl chains on one side of the polymer backbone. The crosslinking agent used in the polymeric composition contains at least two functional groups capable of reacting with the amino groups of the polymer used in the coating. In one example of the crosslinking agent used in the polymeric composition, the crosslinking agent is selected from polyaldehyde crosslinking agents (e.g. monomeric or oligimeric molecules having 2 or more —CHO groups), phosphines having the general formula (A)$_3$P, wherein A is hydroxyalkyl, silanes having 2 or more alkoxy groups, and mixtures thereof. The nitric oxide generating functional groups associated with the crosslinked chemical combination may be any functional groups that release nitric oxide when exposed to bodily fluids.

In one example embodiment, the nitric oxide generating functional groups comprise nitrate groups that are provided by a nitrated compound (e.g., nitrocellulose) imbedded within the crosslinked polymer network structure. Nitrated compounds produce physiologically important levels of nitric oxide. For instance, nitroglycerine or trinitroglycerine has long been used as a way to stave off an impending heart attack that starts with the chest pain medically referred to as angina. Typically, the heart attack victim is given a small tablet of nitroglycerine orally. The victim's own body fluids then convert the nitroglycerine's nitrate groups to nitric oxide. The nitric oxide then dilates the vascular system easing blood flow to the heart and alleviating the angina pain. In a similar manner, this version of a polymeric composition according to the invention releases nitrates which are then converted to nitric oxide in a fluid. In other words, the nitrate functional groups serve to generate nitric oxide.

In another example embodiment, the nitric oxide generating functional groups comprise N$_2$O$_2^-$ groups covalently bonded to amino groups on the crosslinked polymer. In one version of this embodiment, the invention utilizes the reaction between nitric oxide and amines to form a diazeniumdiolate derivative of the crosslinked polymer (i.e., the polymer has N$_2$O$_2^-$ groups). Once exposed to a physiological environment, the coating generates the nitric oxide by releasing nitric oxide through interaction with an available acidic proton. The acidity required is quite mild and simply exposing the polymer to water can trigger this release.

An article capable of generating nitric oxide may be produced by a process according to the invention in which a polymer having at least two amino substituted side chains is mixed with a crosslinking agent to produce a polymer solution. The crosslinking agent contains at least two crosslinking functional groups which react and combine with amino groups on the polymer. A compound having nitric oxide generating functional groups and/or a compound capable of reacting to provide N$_2$O$_2^-$ groups that are covalently or ionically bonded to amino groups on the crosslinked polymer are then added to the polymer solution. The polymer solution is coated on at least a portion of a substrate to produce a crosslinked polymer coating on the substrate. In another version of the invention, a compound capable of reacting to provide N$_2$O$_2^-$ groups bonded to amino groups on the crosslinked polymer is applied to a crosslinked polymer coating already disposed on the substrate.

In an example embodiment of the invention, the versatile chemical methodology of the invention allows for the deposition of an antithrombogenic polymeric composition on a polymeric substrate (e.g., polydimethylsiloxane, polyurethane, and polypropylene). The polymeric composition includes a two dimensional polymer having a backbone of repeating p-amino acid units with long aliphatic side-chain and free —NH and —NH$_2$ substituents and may be synthesized by condensation of 2(5H)-furanone, or maleic acid derivatives (such as anhydride, esters, and so on) with a long-chain amine (e.g., tetradecylamine) and a polyamine (e.g., pentaethylenehexamine, polyethylene imine). Crosslinking of the two-dimensional polymer is undertaken with glutaraldehyde and/or tris(hydroxymethyl)phosphine (the crosslinking agents), and a compound having nitric oxide generating functional groups and/or a compound capable of reacting to provide N$_2$O$_2^-$ groups that are subsequently covalently or ionically bonded to amino groups on the crosslinked polymer are associated with the crosslinked polymer coating. Various mechanisms are available for associating the compound having nitric oxide generating functional groups and/or a compound capable of reacting to provide N$_2$O$_2^-$ groups that are covalently or ionically bonded to amino groups on the crosslinked polymer into the crosslinked polymer coating, such as ionic bonding, covalent bonding and entrapment. However, it should be understood that the invention is not limited by the means for associating the nitric oxide generating functional groups into the crosslinked polymer coating.

It is therefore an advantage of the present invention to provide an antithrombogenic polymeric composition having improved physical properties such that the antithrombogenic polymeric composition may be easily applied to a substrate to produce an article which has excellent antithrombogenic properties and which retains its antithrombogenic properties in a permanent and non-leachable fashion when placed in an environment (e.g., bodily fluids).

It is another advantage of the present invention to provide a process, that efficiently prepares a polymer having side chains with a functional group that readily bonds to nitric oxide generating functional groups such that an antithrombogenic polymer may be prepared from the polymer and a compound that reacts to form nitric oxide generating functional groups on the polymer.

It is yet another advantage of the present invention to provide a process that efficiently prepares a polymer having side chains such that an antithrombogenic polymer may be prepared from the polymer, a crosslinking agent and a compound having nitric oxide generating functional groups that is contained within the crosslinked polymer structure.

These and other features, aspects, and advantages of the present invention will become better understood upon consideration of the following detailed description, drawings, and appended claims.

DETAILED DESCRIPTION OF THE INVENTION

The present invention is directed to a polymeric composition capable of generating nitric oxide when exposed to bodily fluids thereby providing antithrombogenic properties. The polymeric composition comprises (1) a crosslinked chemical combination of (i) a polymer having side chains along a backbone forming the polymer, at least two of the side chains containing an amino group, and (ii) a crosslinking agent containing at least two functional groups capable of reacting with the amino groups; and (2) a plurality of nitric oxide generating functional groups associated with the crosslinked chemical combination. An article according to the invention comprises a substrate and a coating of the polymeric composition disposed on at least a portion of the substrate.

Figure 1A:
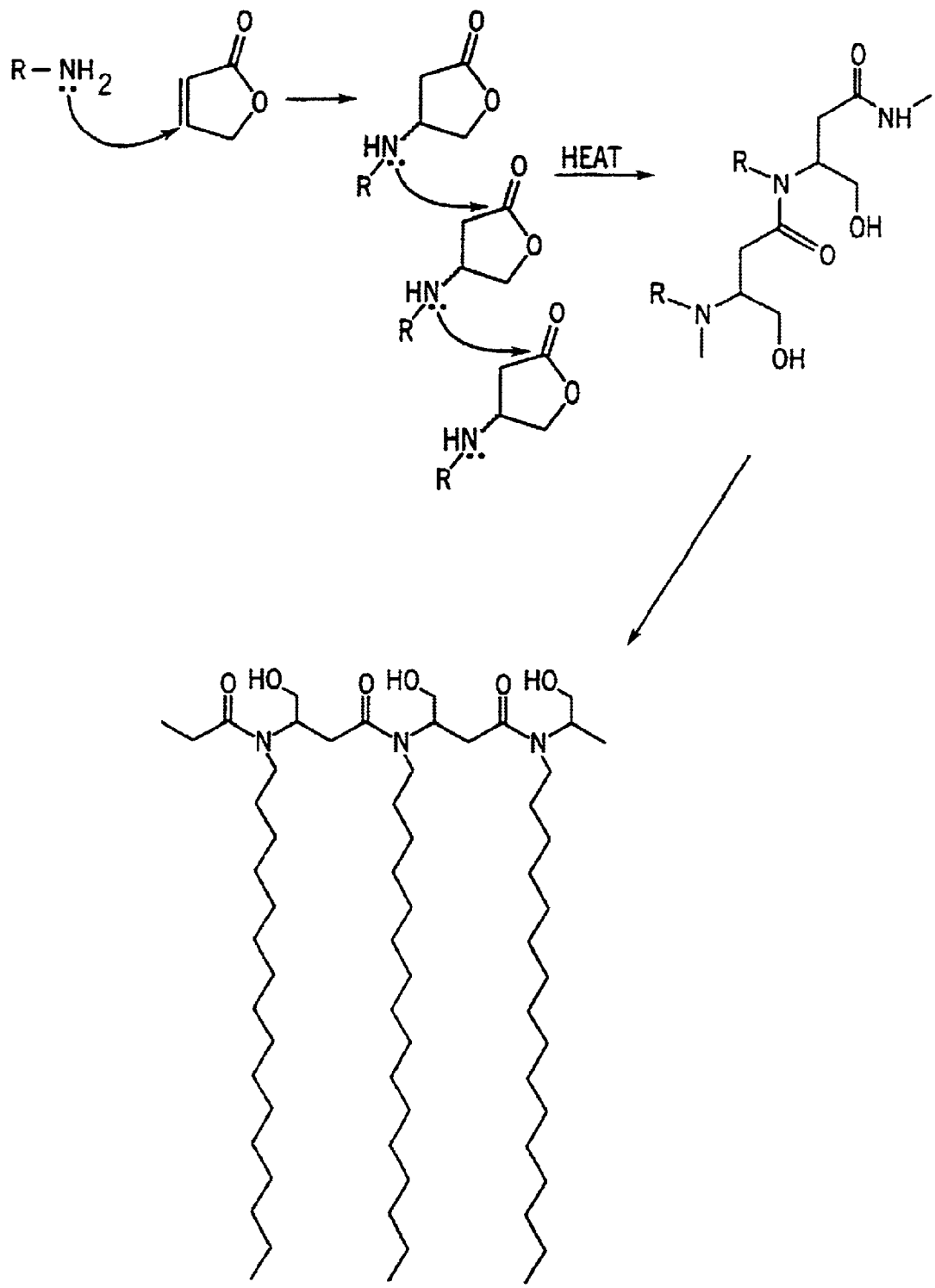
FIG. 1A shows a process for synthesizing a polyamide that is suitable for forming an antithrombogenic polymeric composition coating in accordance with the present invention.
Figure 1B:
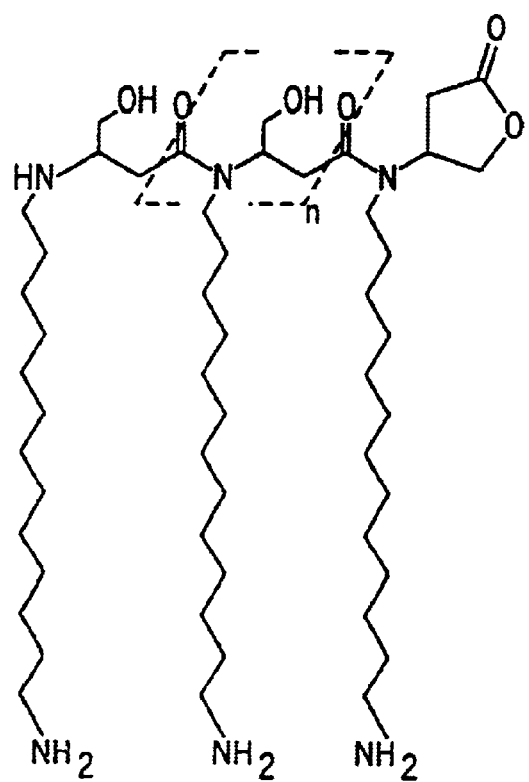
FIG. 1B shows example polyamides having amino groups that are suitable for forming the antithrombogenic polymeric composition coating in accordance with the present invention.
Figure 1B:
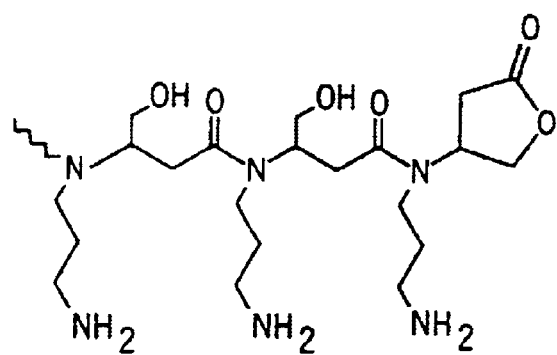

The polymer used in the polymeric composition according to the invention comprises a polymer having side chains along a backbone forming the polymer wherein at least two of the side chains contain an amino group (—NRH, —NH$_2$, —NRH$_2^+$, —NH$_3^+$). In one example embodiment of the polymer, the polymer is a polyamide synthesized using the polymerization reactions disclosed in U.S. Pat. No. 6,153,724, which are shown in FIG. 1A. Looking at FIG. 1A, it can be seen that the polyamide can be synthesized using an α,β-unsaturated gamma lactone, such as 2(5H)-furanone, as an agent to effect the regular, sequential alignment of side chains along a polyamide backbone. The furanone undergoes facile reaction with a primary amine by Michael-type addition to yield α,β-amino gamma lactone which then polymerizes to form a polyamide chain with the pendant side chain. Depending on the side group (R), the method can produce many different types of polyamides. When the R group is selected from fatty alkyl and polyamine (such as pentaethylenehexamine or polyethylene imine), a polymer having fatty alkyl chains and amino substituted alkyl chains on one side of the polymer backbone and hydroxymethyl groups on the other side of the backbone is formed. See FIG. 1B. This example two-dimensional polymer has a backbone of repeating β-amino acid units with fatty alkyl (e.g., tetradecyl) and polyamine (derived from pentaethylenehexamine or polyethylene imine) side chains randomly distributed along the chain. By virtue of its amphithetic properties, the two-dimensional polymers are easily soluble in both water and most organic solvents (e.g., alcohols, tetrahydrofuran, chloroform, toluene, N,N-dimethylformamide, and the like).

One polyamide disclosed in U.S. Pat. No. 6,153,724 and useful in the present invention is formed by reacting an α,β-unsaturated lactone and a first amine to form an intermediate reaction product, wherein the first amine is selected from RR$_1$NH, RNH$_2$, RR$_1$NH$_2^+$, RNH$_3^+$ and mixtures thereof, wherein R and R$_1$ can be the same or different and each contain between about 1 and 50 carbon atoms and are optionally substituted with heteroatoms oxygen, nitrogen, sulfur, and phosphorus and combinations thereof; and (ii) reacting the intermediate reaction product and a polyamine to form the polyamide, wherein the second polyamine is selected from R$_2$R$_3$NH, R$_2$NH$_2$, R$_2$R$_3$NH$_2^+$, R$_2$NH$_3^+$ and mixtures thereof, wherein R$_2$ and R$_3$ can be the same or different and each contain an amino group (—NRH, —NH$_2$, —NRH$_2^+$, —NH$_3^+$) and between about 1 and 50 carbon atoms and are optionally substituted with heteroatoms oxygen, nitrogen, sulfur, and phosphorus and combinations thereof, wherein multiples of the R, R$_1$, R$_2$, and R$_3$ are in a vertically aligned spaced relationship along a backbone formed by the polyamide. In one example embodiment of the invention, R, R$_1$, R$_2$, and R$_3$ may be selected from alkyl, alkenyl, alkynyl, cycloalkyl, aryl, aralkyl, hydroxyl, nitrile, carboxyl, sulfate, phosphate, sulfonyl, trialkylammonium and combinations thereof and optionally can be substituted with a halogen selected from the group consisting of chlorine, iodine, bromine, fluorine and combinations thereof. The R, R$_1$, R$_2$, and R$_3$ groups may be the same or different depending on the desired structure for the final polyamide. In other words, the first amine and the second amine used in the polymerization process may be the same or different. In one embodiment, R and R$_1$ are alkyl and the second amine is a polyalkylene polyamine. In another embodiment, the first amine is tetradecylamine and the polyalkylene polyamine is pentaethylenehexamine. In yet another embodiment, the first amine is tetradecylamine and the polyalkylene polyamine is polyethylene imine. Proper selection of the amines for inclusion in the polymer will create a two-dimensional structure such that one "side" of the polymer is non-polar or lipophilic and the other side of the polymer is polar or hydrophilic, thereby preserving the sidedness of the polymer.

Figure 2A:
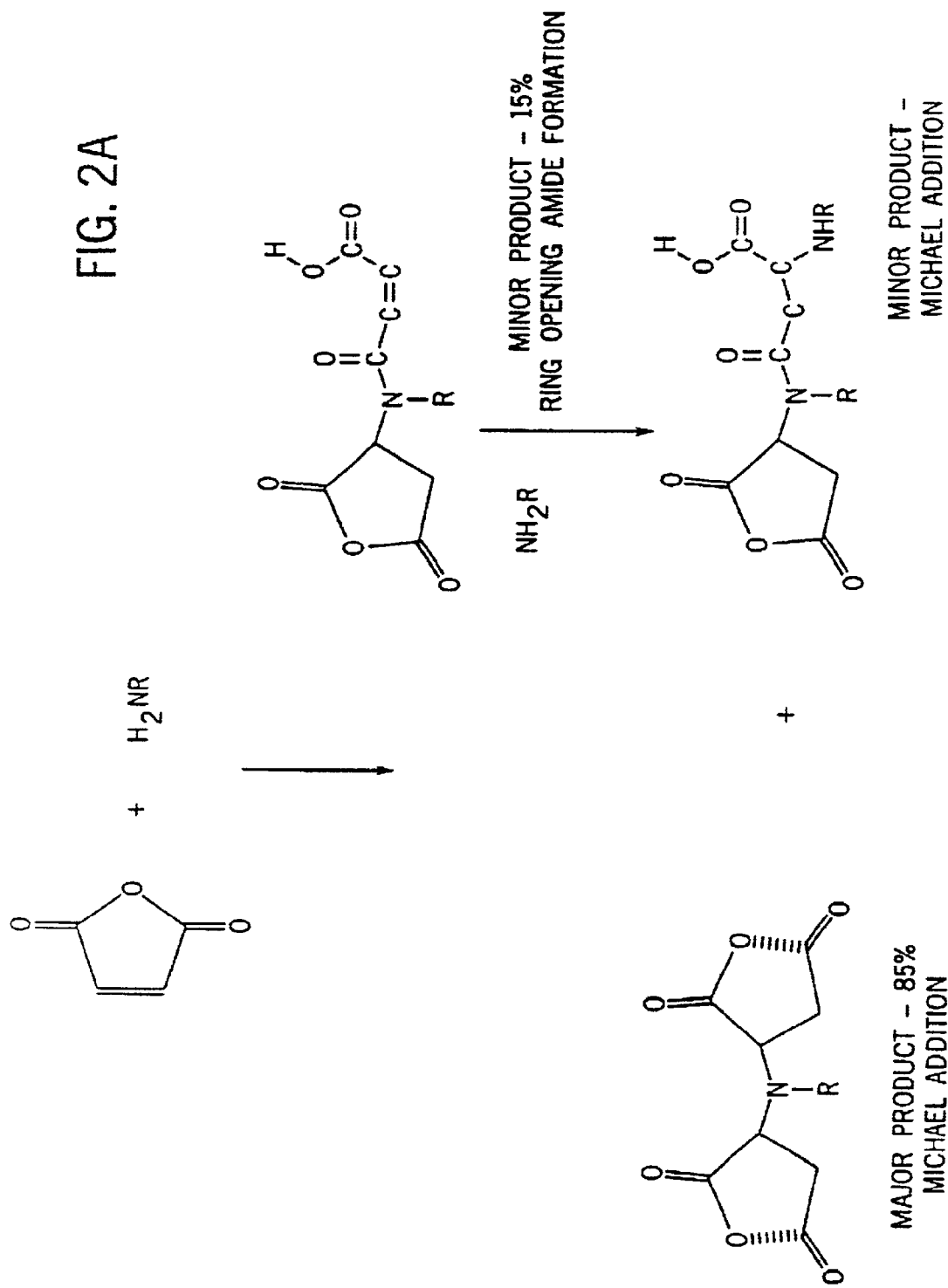
FIGS. 2A and 2B show a process for synthesizing another example polyamide having amino groups that are suitable for forming the antithrombogenic polymeric composition coating in accordance with the present invention.
Figure 2B:
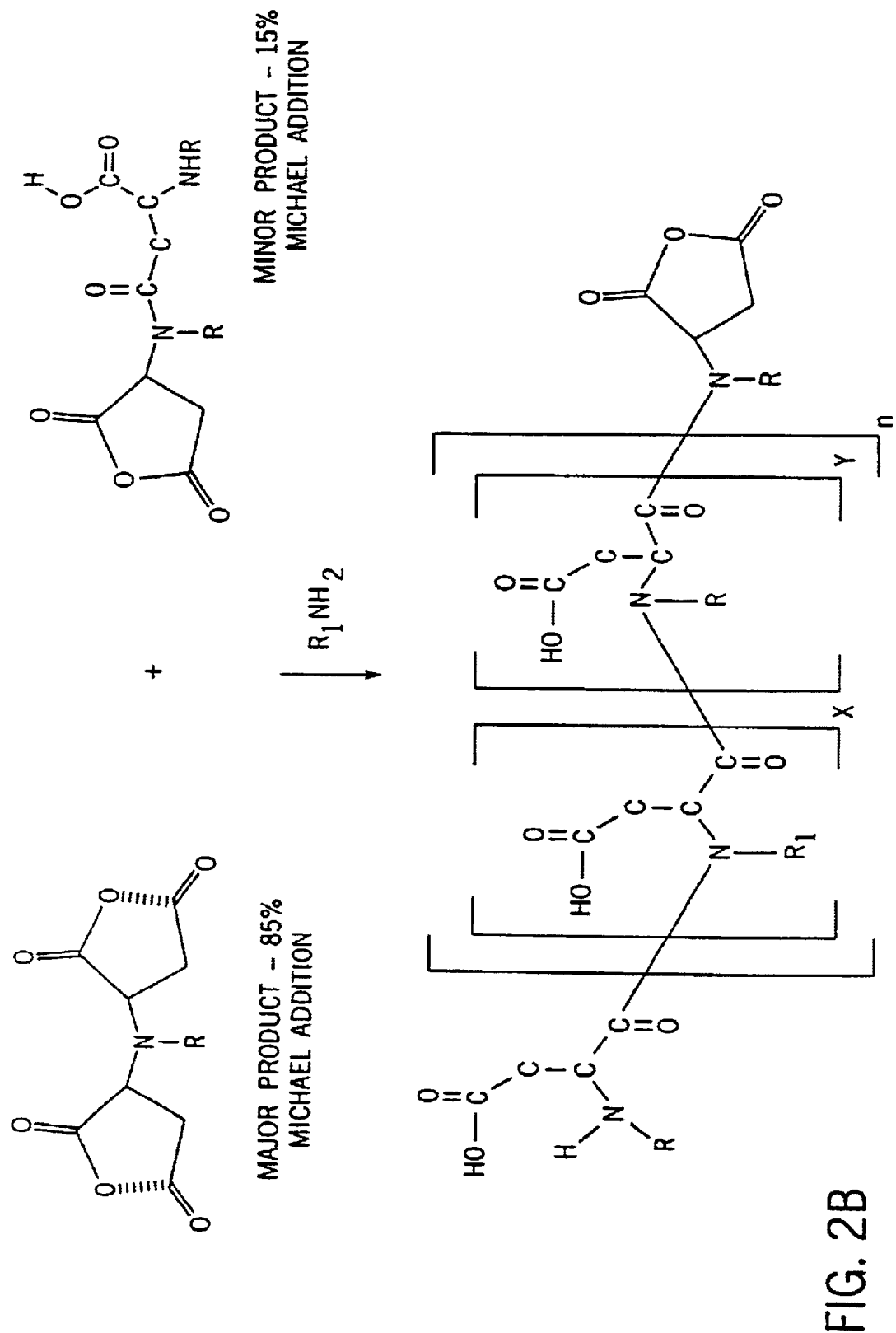

In another example of the polymer used in the polymeric composition according to the invention, the polymer is a polyamide synthesized using the polymerization reaction disclosed in the U.S. patent application Ser. No. 09/698,619 entitled "Two Dimensional Polyamides Prepared from Unsaturated Carboxylic Acids and Amines" filed on Oct. 27, 2000 by William F. McDonald et al., which is owned by the assignee of the present invention and is incorporated herein by reference. In this U.S. Patent Application, there is described a polymerization process in which a monomer selected from unsaturated carboxylic acids, esters of unsaturated carboxylic acids, anhydrides of unsaturated carboxylic acids, and mixtures thereof is reacted with a first amine to form an intermediate reaction product, and then the intermediate reaction product is reacted with a polyamine to form a polyamide wherein at least a portion of the side chains along a backbone forming the polyamide are amino substituted alkyl chains. See FIGS. 2A and 2B (wherein $R_1$ includes an amino group). The process for producing this polyamide involves reacting a monomer selected from unsaturated carboxylic acids, esters of unsaturated carboxylic acids, anhydrides of unsaturated carboxylic acids and mixtures thereof with a first amine to form an intermediate reaction product in the reaction mixture, wherein the first amine is selected from $RR_1NH$, $RNH_2$, $RR_1NH_2^+$, $RNH_3^+$ and mixtures thereof, wherein R and $R_1$ can be the same or different and each contain between about 1 and 50 carbon atoms and are optionally substituted with heteroatoms oxygen, nitrogen, sulfur, and phosphorus and combinations thereof. The reaction of the monomer and the first amine forms an intermediate reaction product in the reaction mixture. The intermediate reaction product is then reacted with a second amine selected from $R_2R_3NH$, $R_2NH_2$, $R_2R_3NH_2^+$, $R_2NH_3^+$ and mixtures thereof, wherein $R_2$ and $R_3$ can be the same or different and each contain an amino group (—NRH, —$NH_2$, —$NRH_2^+$, —$NH_3^+$) and each contain between about 1 and 50 carbon atoms and are optionally substituted with heteroatoms oxygen, nitrogen, sulfur, and phosphorus and combinations thereof. The reaction of the intermediate reaction product with the second amine forms the polyamide in the reaction mixture. The polyamide may then be separated from the reaction mixture. A polyamide produced in accordance with the method of the invention includes multiples of the R, $R_1$, $R_2$, and $R_3$ groups in vertically aligned spaced relationships along a backbone formed by the polyamide.

Suitable unsaturated carboxylic acids, esters of unsaturated carboxylic acids, and anhydrides of unsaturated carboxylic acids for use as the monomer in this, polymerization process have for example from 3 to 18 carbon atoms in the molecule. Of this group of acids, the monocarboxylic acid, acrylic acid, and the dicarboxylic acid, maleic acid, are preferred. Of this group of esters, maleic acid monoesters (such as maleic acid monoethyl ester) are preferred. A non-limiting example of anhydrides of the unsaturated carboxylic acids is maleic anhydride. In one example embodiment of the invention, R, $R_1$, $R_2$, and $R_3$ may be selected from alkyl, alkenyl, alkynyl, cycloalkyl, aryl, aralkyl, hydroxyl, nitrile, carboxyl, sulfate, phosphate, sulfonyl, trialkylammonium and combinations thereof and optionally can be substituted with a halogen selected from the group consisting of chlorine, iodine, bromine, fluorine and combinations thereof. The R, $R_1$, $R_2$, and $R_3$ groups may be the same or different depending on the desired structure for the final polyamide. In other words, the first amine and the second amine used in the polymerization process may be the same or different. In one embodiment, R and $R_1$ are alkyl and the second amine is a polyalkylene polyamine. In another embodiment, the first amine is tetradecylamine and the polyalkylene polyamine is pentaethylenehexamine. In yet another embodiment, the first amine is tetradecylamine and the polyalkylene polyamine is polyethylene imine. Proper selection of the amines for inclusion in the polymer will create a two-dimensional structure such that one "side" of the polymer is non-polar or lipophilic and the other side of the polymer is polar or hydrophilic, thereby preserving the sidedness of the polymer.

In another example of the polymer used in the antimicrobial polymeric composition, the polymer is a polyamide synthesized using the polymerization reaction disclosed in U.S. patent application Ser. No. 09/698,619 entitled "Two Dimensional Polyamides Prepared from Unsaturated Carboxylic Acids and Amines" filed on Oct. 27, 2000 by William F. McDonald et al., issued as U.S. Pat. No. 6,495,657 which is owned by the assignee of the present invention and is incorporated herein by reference. In this U.S. patent application, there is described a polymerization process in which a monomer selected from unsaturated carboxylic acids, esters of unsaturated carboxylic acids, anhydrides of unsaturated carboxylic acids, and mixtures thereof is reacted with a first amine to form an intermediate reaction product, and then the intermediate reaction product is reacted with a polyamine to form a polyamide wherein at least a portion of the side chains along a backbone forming the polyamide are amino substituted alkyl chains. See FIGS. 2A and 2B (wherein $R_1$ includes an amino group). The process for producing this polyamide involves reacting a monomer selected from unsaturated carboxylic acids, esters of unsaturated carboxylic acids, anhydrides of unsaturated carboxylic acids and mixtures thereof with a first amine to form an intermediate reaction product in the reaction mixture, wherein the first amine is selected from $RR_1NH$, $RNH_2$, $RR_1NH_2^+$, $RNH_3^+$ and mixtures thereof, wherein R and $R_1$ can be the same or different and each contain between about 1 and 50 carbon atoms and are optionally substituted with heteroatoms oxygen, nitrogen, sulfur, and phosphorus and combinations thereof. The reaction of the monomer and the first amine forms an intermediate reaction product in the reaction mixture. The intermediate reaction product is then reacted with a second amine selected from $R_2R_3NH$, $R_2NH_2$, $R_2R_3NH_2^+$, $R_2NH_3^+$ and mixtures thereof, wherein $R_2$ and $R_3$ can be the same or different and each contain an amino group (—NRH, —$NH_2$, —$NRH_2^+$, —$NH_3^+$) and each contain between about 1 and 50 carbon atoms and are optionally substituted with heteroatoms oxygen, nitrogen, sulfur, and phosphorus and combinations thereof. The reaction of the intermediate reaction product with the second amine forms the polyamide in the reaction mixture. The polyamide may then be separated from the reaction mixture. A polyamide produced in accordance with the method of the invention includes multiples of the R, $R_1$, $R_2$, and $R_3$ groups in vertically aligned spaced relationships along a backbone formed by the polyamide.

The example polyamides can also be crosslinked using a phosphine crosslinking agent having the general formula $(A)_3P$ and mixtures thereof, wherein A is hydroxyalkyl. The A groups of the phosphine crosslinking agent undergo a spontaneous Mannich-type reaction with amino groups on the polymer under mild conditions (pH~7, aqueous or organic media, room temperature, 2–24 hours). This results in the formation of an aminomethyl-phosphine linkage (N—$CH_2$—P—$CH_2$—N) which is much less susceptible to enzyme deactivation and hydrolysis at a low pH than other known crosslinkages. The phosphine crosslinking agent has many other important features. For example, the phosphine crosslinking agent has a high reactivity to amino groups under mild conditions (room temperature, in aqueous or organic media, pH 2–9, and a pot life extending to several hours). The resulting Mannich base type products formed from the phosphine crosslinking agent show a higher stability over that provided by glutaraldehyde in that a polymer crosslinked by glutaraldehyde containing 10% phosphine crosslinking agent was found to withstand low pH (pH 2–3) and high temperature conditions (boiling water poured into a large beaker followed by the addition of the coated plates without additional heating for 30 minutes) without deterioration. The phosphine crosslinking agent offers the benefits of operational simplicity, good biocompatibility, and low cost. The phosphine crosslinking agent can also react with the substrate to create tightly bound anchors between the polyamide coating and the substrate. Non-limiting examples of phosphine crosslinking agents include tris (hydroxymethyl)phosphine, tris(1-hydroxyethyl)phosphine, and tris(1-hydroxypropyl)phosphine. In certain circumstances, it may be cost effective to form the phosphine crosslinking agent in situ such as by the reaction of tetrakis(hydroxymethyl)phosphonium chloride and triethylamine. The amount of crosslinking agent and the amount of polymer used to produce the polymeric composition can be varied depending upon the particular crosslinking agent utilized, the reaction conditions and the particular product application contemplated. For example, the ratio of A groups in the phosphine crosslinking agent to the total of amount of amino groups in the polyamide can be varied to achieve a predetermined level of crosslinking.

Other crosslinking agents may also be used to crosslink the example polyamides. Other non-limiting examples include dialkoxy, trialkoxy, and tetraalkoxy silanes (i.e., silanes having 2 or more alkoxy groups such as triethoxysilane, triethoxymethylsilane, diethoxymethyloctadecylsilane, and diethoxymethylsilane), tetraalkoxy titanium, diisocyanates (both alkyl and aryl), and dianhydrides.

The nitric oxide generating functional groups in the polymeric composition may be provided by physically imbedding compounds including nitric oxide generating functional groups in the polymeric composition or by chemically bonding nitric oxide generating functional groups to the polymeric composition. In one embodiment, the nitric oxide generating functional groups comprise nitrate groups that are provided by a nitrated compound (e.g., nitrocellulose) imbedded within the crosslinked polymer network structure. Upon release in fluids, the nitrate groups convert to (i.e., generate) nitric oxide. In another example embodiment, the nitric oxide generating functional groups comprise $N_2O_2^-$ groups covalently or ionically bonded to amino groups on the crosslinked polymer. The covalent bonding of $N_2O_2^-$ groups to amino groups on the crosslinked polymer can be achieved by reacting the non-crosslinked or crosslinked polymer having amino groups with nitric oxide (N=O). Nitric oxide has many biological effects, and its site-specific delivery has many uses including, for example, vasodilation and inhibition of platelet aggregation. As shown below, two nitric oxide (N=O) molecules can bind to an amino group on the polymer to form a diazeniumdiolate.

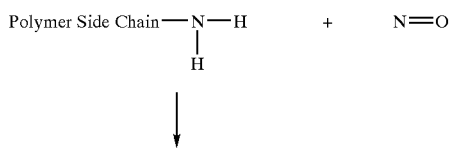

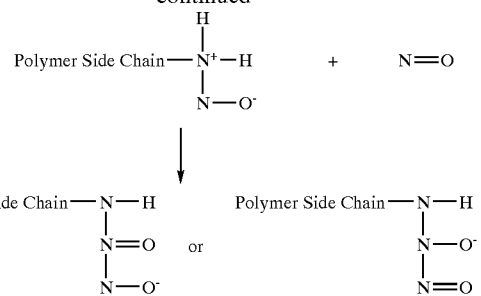

Once exposed to a physiological environment, the $N_2O_2^-$ groups that are covalently bonded to amino groups on the polymer release (i.e., generate) nitric oxide through interaction with an available acidic proton. The acidity required is quite mild and simply exposing the polymer to water can trigger this release. Under appropriate physiological conditions, the NO dissociates from the carrier, and the pharmacological delivery is then complete.

The amount and/or type of the nitric oxide generating functional groups associated with the crosslinked polymer used will vary depending on the particular material employed and ultimate desired effect. For instance, the amount and/or type of the nitric oxide generating functional groups associated with the crosslinked polymer used in a particular application may vary depending on the size of the antithrombogenic surface desired on an article. While the amount and/or type of the nitric oxide generating functional groups associated with the crosslinked polymer used to coat an article may vary to some extent, the amount and/or type of the nitric oxide generating functional groups associated with the crosslinked polymer must be at least a sufficient amount to generate an effective concentration of nitric oxide or nitrate (which thereafter converts to nitric oxide) to inhibit thrombus formation on a surface in contact with bodily fluids. Thus, the term "effective concentration" means a sufficient amount to generate an effective concentration of nitric oxide to inhibit thrombus formation on a surface in contact with bodily fluids. The amount will vary and it is within the skilled artisan's ability to relatively easily determine an effective concentration.

The antithrombogenic polymeric composition, may be applied to any substrate that is considered useful in applications where antithrombogenic properties are advantageous. For instance, an article having antithrombogenic properties and useful as a medical device may include a substrate comprising a polymeric material conventionally used to fabricate articles commonly used in contact with bodily fluids. In this example, a suitable polymeric material may be selected from polyolefins, polyacrylics, polyvinyl chloride, polyamides, polyurethanes, polyurethaneureas, silicone urethane copolymers, polyvinylpyrrolidone, polyvinyl alcohols, cellulosic materials, polystyrene, polyesters, fluorinated polymers, silicone polymers, natural rubber, polycarbonates, and mixtures thereof. The particular substrate selected does not constitute a critical aspect of the invention other than to serve as a support substrate for the antithrombogenic polymeric coating composition.

An article having an antithrombogenic surface according to the invention may be prepared using various methods as follows. In a first method for preparing an article having an antithrombogenic surface according to the invention, the substrate is precleaned, if necessary, and the surface of the substrate is modified via coupling agent, if necessary. A solution of the polymer having side chains along a backbone forming the polymer wherein at least two of the side chains contain an amino group (—NRH, —NH$_2$, —NRH$_2{}^+$, —NH$_3{}^+$) is then prepared in a suitable solvent, such as isopropanol. The polymer concentration can vary and is typically from 1 to 5% depending on the desired coating concentration.

A crosslinking agent or a mixture of crosslinking agents is then added to the polymer solution. Each crosslinking agent should contain at least two functional groups capable of reacting with the amino groups of the polymer. Non-limiting examples of crosslinking agents include polyaldehydes, such as glutaraldehyde, phosphines having the general formula (A)$_3$P, wherein A is hydroxyalkyl, and mixtures thereof. One example mixture of crosslinking agents includes glutaraldehyde and tris(hydroxymethyl) phosphine. The phosphine crosslinking agent may also be formed in situ such as by the reaction of tetrakis (hydroxymethyl)phosphonium chloride and triethylamine. A compound having nitric oxide generating functional groups or a mixture of compounds having nitric oxide generating functional groups are then added to the polymer solution. In one example embodiment, the nitric oxide generating functional groups comprise nitrate groups that are provided by a nitrated compound (e.g., nitrocellulose).

The solution of polymer and crosslinking agent and compound having nitric oxide generating functional groups is then applied to a substrate and the substrate may be heated or baked in an oven at 125° C. for one hour to complete the crosslinking process and create a crosslinked polymeric coating on the substrate. This step may be repeated if necessary. Typically, the coatings are applied using a dipping process. However, the coatings can be spin coated, brushed, sprayed, sponged, or the like onto the substrate. As a result, a compound having nitric oxide generating functional groups is entrapped in the crosslinked polymer coating on the substrate surface.

In a second method for preparing an article having an antithrombogenic surface according to the invention, the substrate is precleaned, if necessary, and the surface of the substrate is modified via coupling agent, if necessary. A solution of the polymer having side chains along a backbone forming the polymer wherein at least two of the side chains contain an amino group (—NRH, —NH$_2$, —NRH$_2{}^+$, —NH$_3{}^+$) is then prepared in a suitable solvent, such as isopropanol. The polymer concentration can vary and is typically from 1 to 5% depending on the desired coating concentration.

A crosslinking agent or a mixture of crosslinking agents is then added to the polymer solution. Each crosslinking agent should contain at least two functional groups capable of reacting with the amino groups of the polymer. Non-limiting examples of crosslinking agents include polyaldehydes, such as glutaraldehyde, phosphines having the general formula (A)$_3$P, wherein A is hydroxyalkyl, and mixtures thereof. One example mixture of crosslinking agents includes glutaraldehyde and tris(hydroxymethyl) phosphine. The phosphine crosslinking agent may also be formed in situ such as by the reaction of tetrakis (hydroxymethyl)phosphonium chloride and triethylamine. A compound capable of reacting to provide N$_2$O$_2{}^-$ groups that are covalently bonded to amino groups on the polymer is then contacted with the polymer solution. Nitric oxide (N═O) is a suitable compound capable of reacting to provide N$_2$O$_2{}^-$ groups that are covalently bonded to amino groups on the polymer. Alternatively, the compound capable of reacting to provide N$_2$O$_2{}^-$ groups that are covalently bonded to amino groups on the polymer is reacted with the polymer before the polymer is placed in solution with a cross-linking agent.

The solution is then applied to a substrate and the substrate may be heated or baked in an oven at 125° C. for one hour to complete the crosslinking process and create a crosslinked polymeric coating on the substrate. This step may be repeated if necessary. Typically, the coatings are applied using a dipping process. However, the coatings can be spin coated, brushed, sprayed, sponged, or the like onto the substrate. A crosslinked polymer coating having nitric oxide generating N$_2$O$_2{}^-$ groups that are covalently bonded to amino groups on the polymer is formed.

Once exposed to a physiological environment, the N$_2$O$_2{}^-$ groups that are covalently bonded to amino groups on the polymer release (i.e., generate) nitric oxide through interaction with an available acidic proton. The acidity required is quite mild and simply exposing the polymer to water can trigger this release. In other words, the N$_2$O$_2{}^-$ functional groups that are bound to the amino groups on the polymer generally are capable of generating nitric oxide in an aqueous environment spontaneously upon contacting the aqueous environment.

In a third method for preparing an article having an antithrombogenic surface according to the invention, the substrate is precleaned, if necessary, and the surface of the substrate is modified via coupling agent, if necessary. A solution of the polymer having side chains along a backbone forming the polymer wherein at least two of the side chains contain an amino group (—NRH, —NH$_2$, —NRH$_2{}^+$, —NH$_3{}^+$) is then prepared in a suitable solvent, such as isopropanol. The polymer concentration can vary and is typically from 1 to 5% depending on the desired coating concentration.

A crosslinking agent or a mixture of crosslinking agents is then added to the polymer solution. Each crosslinking agent should contain at least two functional groups capable of reacting with the amino groups of the polymer. Non-limiting examples of crosslinking agents include polyaldehydes, such as glutaraldehyde, phosphines having the general formula (A)$_3$P, wherein A is hydroxyalkyl, and mixtures thereof. One example mixture of crosslinking agents includes glutaraldehyde and tris(hydroxymethyl) phosphine. The phosphine crosslinking agent may also be formed in situ such as by the reaction of tetrakis (hydroxymethyl)phosphonium chloride and triethylamine.

The polymer/crosslinking agent solution is then applied to a substrate and the substrate may be heated or baked in an oven at 125° C. for one hour to complete the crosslinking process and create a crosslinked polymeric coating on the substrate. This step may be repeated if necessary. Typically, the coatings are applied using a dipping process. However, the coatings can be spin coated, brushed, sprayed, sponged, or the like onto the substrate. A crosslinked polymer coating is formed on the substrate.

The crosslinked polymer coating on the substrate is then contacted with a compound capable of reacting to provide N$_2$O$_2{}^-$ groups that are covalently bonded to amino groups on the crosslinked polymer coating. Nitric oxide (N═O) is a suitable compound capable of reacting to provide N$_2$O$_2{}^-$ groups that are covalently bonded to amino groups on the crosslinked polymer coating. A crosslinked polymer coating having N$_2$O$_2{}^-$ groups that are covalently bonded to amino groups on the crosslinked polymer is then formed. Once exposed to a physiological environment, the N$_2$O$_2{}^-$ groups that are covalently bonded to amino groups on the polymer release (i.e., generate) nitric oxide through interaction with an available acidic proton. The acidity required is quite mild and simply exposing the polymer to water can trigger this release. In other words, the $N_2O_2^-$ functional groups that are bound to the amino groups on the polymer generally are capable of generating nitric oxide in an aqueous environment spontaneously upon contacting an aqueous environment.

EXAMPLES

The following examples serve to further illustrate the invention. The examples are not intended to limit the invention in any way.

Example 1a

Preparation of a Polyamide with Side Chains

A polymer with side chains was prepared as follows. First, 1.0 moles (144.1 grams) of maleic acid mono-ethyl ester was dissolved in 100 grams of isopropanol in a break away resin kettle. The kettle containing the maleic acid mono-ethyl ester/isopropanol solution was then cooled in an ice bath with agitation. Second, 0.5 moles (160.7 grams) of commercially available tetradecylamine was dissolved in 250 grams of isopropanol and added slowly to the cooled maleic acid mono-ethyl ester solution with stirring. A Michael-type addition reaction product began to precipitate within 5 minutes. The tetradecylamine addition required about two hours with ice bath conditions being maintained throughout. Third, 58.1 grams (0.25 moles) of commercially available pentaethylenehexamine were added drop wise to the reaction solution over a two hour period. The reaction is removed from the ice bath at the end of the monomer addition and stirred for an additional 2 hours. The amount of pentaethylene-hexamine charged is determined from the monomer charge from the formation of intermediate. After complete addition of the pentaethylene-hexamine, the reaction kettle was removed from the cold bath with continuous stirring for another 2 hours.

Example 1b

Preparation of Another Polyamide with Side Chains

A polymer with side chains was prepared as follows. First, 1.0 moles (144.1 grams) of maleic acid mono-ethyl ester was dissolved in 100 grams of isopropanol in a break away resin kettle. The kettle containing the maleic acid mono-ethyl ester/isopropanol solution was then cooled in an ice bath with agitation. Second, 0.5 moles (160.7 grams) of commercially available tetradecylamine was dissolved in 250 grams of isopropanol and added slowly to the cooled maleic acid mono-ethyl ester solution with stirring. A Michael-type addition reaction product began to precipitate within 5 minutes. The tetradecylamine addition required about two hours with ice bath conditions being maintained throughout. Third, commercially available polyethylene imine (molecular weight≈600) were added drop wise to the reaction solution over a two hour period. The reaction is removed from the ice bath at the end of the monomer addition and stirred for an additional 2 hours. The amount of polyethylene imine charged is determined from the monomer charge from the formation of intermediate. After complete addition of the polyethylene imine, the reaction kettle was removed from the cold bath with continuous stirring for another 2 hours.

Example 2

Preparation of a Substrate

Before application of a polymer coating to a substrate, the surface of the substrate was modified. Substrate surface modification was accomplished by adding 2 milliliters of 3-(2-(2-aminoethylamino)ethylamino)propyl-trimethoxysilane and 0.1 milliliters of glacial acetic acid to 50 milliliters of isopropanol. A polydimethylsiloxane substrate was then dip coated in this solution followed by a 125° C. cure cycle in a forced air oven for 15 minutes.

Example 3

Preparation of a Substrate Having a Nitric Oxide Releasing Polyamide Coating

A 9% solution of the polyamide with side chains prepared in Example 1a was prepared in a 90% isopropanol –10% acetone solution. A polymer coating solution was then prepared by mixing 30 milliliters of the 9% solution of the polyamide, 1 gram nitrocellulose (cellulose nitrate), 3 milliliters of 50% glutaraldehyde, 50 milliliters isopropanol, 3 milliliters of triethylamine, and 1 milliliter of 80% tetrakis (hydroxymethyl)-phosphonium chloride. The surface modified substrates prepared above in Example 2 were then dipped in the polymer coating solution two times and heated by hot air at 120°–150° C. for 1 minute after each dip. The coated substrates were then hung in a 125° C. forced air oven to cure for 1 hour.

Example 4

Testing of Coated Substrates of Example 3 for Nitrate Release

The polyamide coated substrates produced in Example 3 were tested for nitrate release. The coated substrates were subjected to the nitrate test produced by the Nitrate Elimination Company, Inc. (NECI). This assay uses an enzyme and a colorimetric reagent to determine the nitric oxide generated from the coating and stoichiometrically converted to nitrate and nitrite. The test results showed the coated substrates releasing 1.2 to 1.4 ppm nitrate per $cm^2$.

Example 5

Preparation of a Substrate Having a Nitric Oxide Releasing Polyamide Coating

A 9.5% solution of the polyamide-with side chains prepared in Example 1a was prepared in a 90% isopropanol –10% acetone solution. A polymer coating solution was then prepared by mixing 35 milliliters of the 9.5% solution of the polyamide, 1 gram nitrocellulose (cellulose nitrate), 30 milliliters isopropanol, 2 milliliters dimethylaminopyridine, 0.2 milliliters of Triton™ X-100 brand non-ionic surfactant, 1.5 milliliters of 50% glutaraldehyde, 0.25 milliliters of triethylamine, and 0.4 milliliters of 80% tetrakis (hydroxymethyl)-phosphonium chloride. The surface modified substrates prepared above in Example 2 were then dipped in the polymer coating solution two times and heated by hot air at 120°–150° C. for 1 minute after each dip. The coated substrates were then hung in a 125° C. forced air oven to cure for 1 hour.

Example 6

Preparation of a Substrate Having a Nitric Oxide Releasing Polyamide Coating

A 9.5% solution of the polyamide with side chains prepared in Example 1a was prepared in a 90% isopropanol –10% acetone solution. A polymer coating solution was then prepared by mixing 30 milliliters of the 9.5% solution of the polyamide, 1 gram nitrocellulose (cellulose nitrate), 10 milliliters isopropanol, 0.2 milliliters of Triton™ X-100 brand non-ionic surfactant, 1.5 milliliters of 50% aqueous glutaraldehyde, 0.25 milliliters of triethylamine, and 0.4 milliliters of 80% tetrakis(hydroxymethyl)-phosphonium chloride. The surface modified substrates prepared above in Example 2 were then dipped in the polymer coating solution two times and heated by hot air at 120°–150° C. for 1 minute after each dip. The coated substrates were then hung in a 125° C. forced air oven to cure for 1 hour.

Example 7a

Synthesis of a Nitric Oxide Containing Polymer

The polymer of Example 1a was dissolved in the ratio of 5 grams of polymer to 100 milliliters of carbon disulfide in a round bottom flask. A glass tube (Pasteur pipette) or a gas dispersion tube was fitted in a plastic stopper and a nitric oxide tank was attached through the use of an appropriate regulator and a siloxane tube. The polymer carbon disulfide solution was continuously stirred and the nitric oxide line was set to no more than 10 psi and allowed to bubble into the polymer—carbon disulfide solution. The solution with nitric oxide took on an orange hue and eventually began to precipitate from solution. After 2 hours of nitric oxide bubbling, the gas line was shut off and the stirring stopped. The nitric oxide containing polymer was then recovered via roto-evaporation. The infrared data indicates a sharp loss of amine groups through the N—H stretching mode observed at or near 3300 $cm^{-1}$. Yields are typically 80–85%.

Example 7b

Synthesis of Another Nitric Oxide Containing Polymer

The polymer of Example 1b was dissolved in the ratio of 5 grams of polymer to 100 milliliters of carbon disulfide in a round bottom flask. A glass tube (Pasteur pipette) or a gas dispersion tube was fitted in a plastic stopper and a nitric oxide tank was attached through the use of an appropriate regulator and a siloxane tube. The polymer carbon disulfide solution was continuously stirred and the nitric oxide line was set to no more than 10 psi and allowed to bubble into the polymer—carbon disulfide solution. The solution with nitric oxide took on an orange hue and eventually began to precipitate from solution. After 2 hours of nitric oxide bubbling, the gas line was shut off and the stirring stopped. The nitric oxide containing polymer was then recovered via roto-evaporation.

Example 8

Preparation of a Substrate Having a Nitric Oxide Releasing Crosslinked Polyamide Coating A 4% solution of the polyamide with side chains prepared in Example 1a was prepared in a 90% isopropanol –10% acetone solution. A polymer coating solution was then prepared by mixing 50 milliliters of the 4% solution of the polyamide, 0.1 gram of Triton™ X-100 brand non-ionic surfactant, 1.5 milliliters of 50% glutaraldehyde, 0.25 milliliters of triethylamine, 0.4 milliliters of 80% tetrakis (hydroxymethyl)-phosphonium chloride, 0.5 grams of the polymer prepared in Example 7a, and 10 milliliters water. The surface modified substrates prepared above in Example 2 were then dipped in the polymer coating solution two times and heated by hot air at 120°–150° C. for 1 minute after each dip. The coated substrates were then hung in a 125° C. forced air oven to cure for 1 hour.

Example 9

A. Background on Test Methods for Quantifying Nitric Oxide Release

The nitric oxide (NO) produced in body tissues and fluids results in residual nitrate. Nitric oxide produced in response to infection and stress raises the nitrate level over that normally found in the serum. This is due to conversion of nitric oxide to nitrate and nitrite. Low levels of nitrate in serum are normal due to hormonal nitric oxide production and dietary intake. However, when the body is being challenged, the nitric oxide is often produced and results in an elevated level of nitrate, which can be viewed as an indicator of increased production of nitric oxide. In research studies following nitric oxide levels, the transiently produced nitric oxide gas is difficult to detect unless expensive instrumentation is available. Since nitric oxide is stoichiometrically converted to nitrate and nitrite, the levels of the nitric oxide produced in a response can be tracked by assaying for nitrate and nitrite. Converting it to nitrite by enzymatic reduction catalyzed by nitrate reductase does the easiest test for nitrate. The nitrite is detected by a simple colorimetric assay using the Griess Reagents. This approach works well in tissue culture based studies and isolated body tissues and fluids.

B. Testing for Nitric Oxide Release

The substrates produced in Examples 5, 6 and 8 above were tested for nitric oxide release. In particular, the ppm of nitrate per coated substrate area of 0.5×0.5 $cm^2$ was measured and is shown in Table 1.

TABLE 1

| Experimental Conditions | Example 5 | | Example 6 | | Example 8 | |
|---|---|---|---|---|---|---|
| No wash | 0.81 ppm | 13.48 ppm | 14.73 ppm | 10.77 ppm | 4.05 ppm | 4.39 ppm |
| 2 hour wash | 1.14 ppm | 1.12 ppm | 0.77 ppm | 13.41 ppm | 1.05 ppm | 0.92 ppm |
| 24 hour wash | 0.43 ppm | 0.49 ppm | 0.64 ppm | 0.66 ppm | 0.8 ppm | 1.09 ppm |

Example 5 and 6 provide a high nitric oxide source, but taper off quickly. Example 8 (the nitric oxide incorporated into the polymer) does not have as high of initial levels, but is more consistent. The units above are ppm or mg/L. These units are converted to mM or mM per unit area in order to compare the results more directly with other results reported in the literature. Typically, other studies report the detection of x mM or y $\mu$M nitric oxide using the Greiss reagents or other known approaches such as electrochemical. In the present study, the ppm number has been converted to $\mu$g/ml. (ppm) and then to $\mu$moles/ml. which is equivalent to $\mu$M. The actual nitric oxide emission is 0.15 $\mu$M/$cm^2$ using the 4.39 ppm for the Example 8 polymer.

Figure 3:
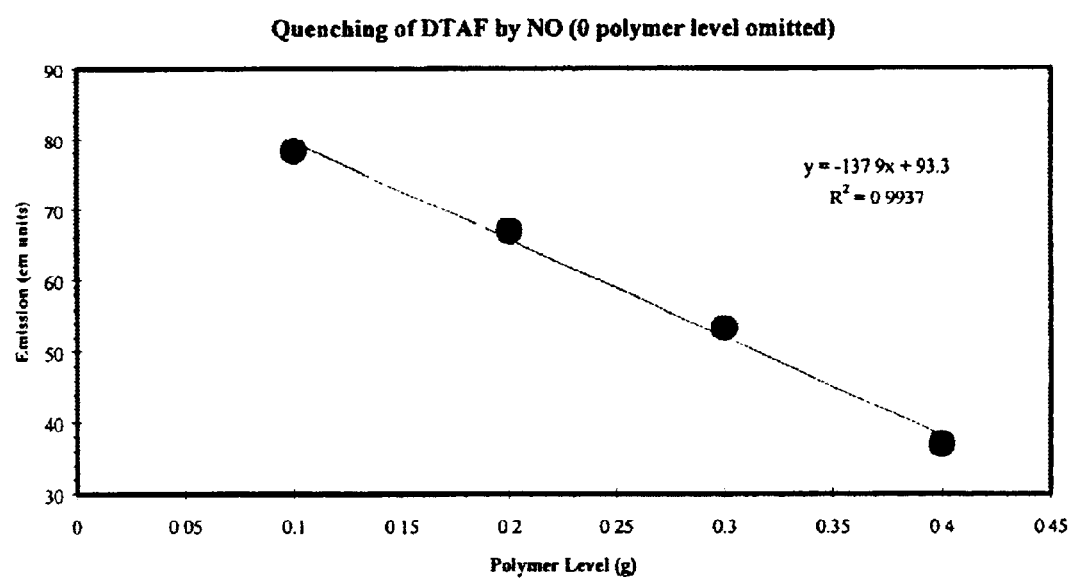
FIG. 3 is a graph illustrating the release of nitric oxide from a polymer according to the invention as measured by the quenching of a fluorophore dye after the dye is exposed to nitric oxide that is driven off of the polymer in an aqueous solution.

The nitric oxide level was also determined through a fairly simple fluorescence measurement by using a fluorophore that contains a free amine group such as 5-(4,6-dichlorotriazinyl)aminofluoroscein (DTAF). The addition of nitric oxide to the DTAF causes quenching and concomitant reduction in the emission of the dye. The dye is excited at 488 nanometers using a xenon lamp and a Perkin Elmer brand scanning fluorimeter. The fluorescent quenching of the dye with nitric oxide is shown in Table 2 below. FIG. 3 illustrates the quenching of the dye once exposed to nitric oxide as it is driven off of the polymer coating on the substrate prepared in Example 8 in an aqueous solution.

TABLE 2

Fluorescent Quenching of the Dye with Nitric Oxide

| Sample | Sample Weight | Fluorescence (Emission) |
|---|---|---|
| Substrate of Example 6 | 0.22 grams | 77 |
| Substrate of Example 8 | 0.32 grams | 95 |
| DTAF only | 100 µl/10 ml isopropanol | 149 |
| Substrate without Nitric Oxide | 0.5 g in 10 ml isopropanol | 149 |

Example 10

Figure 4:
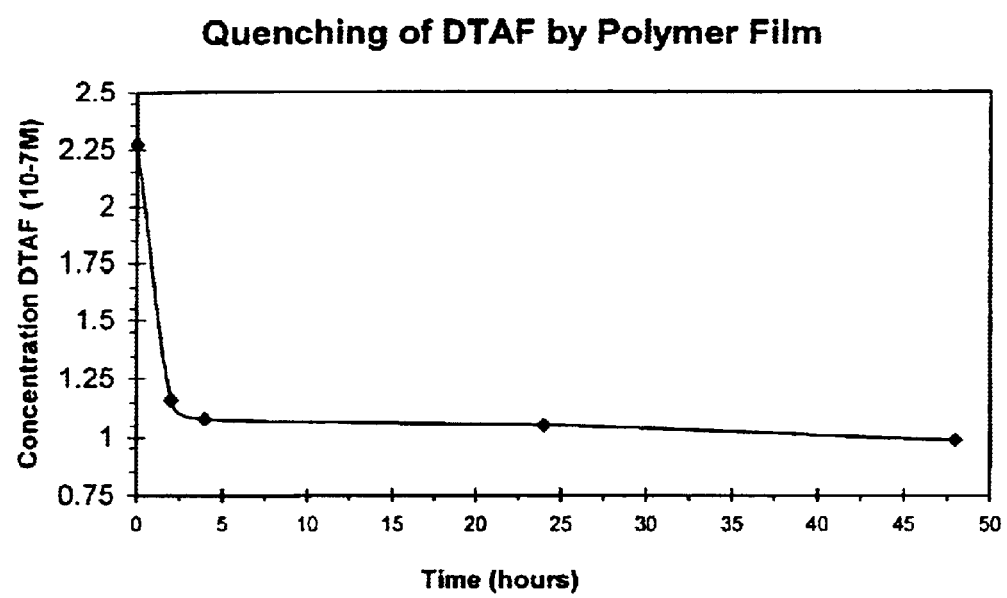
FIG. 4 is a graph illustrating quenching of DTAF by the polymer film.
Figure 5:
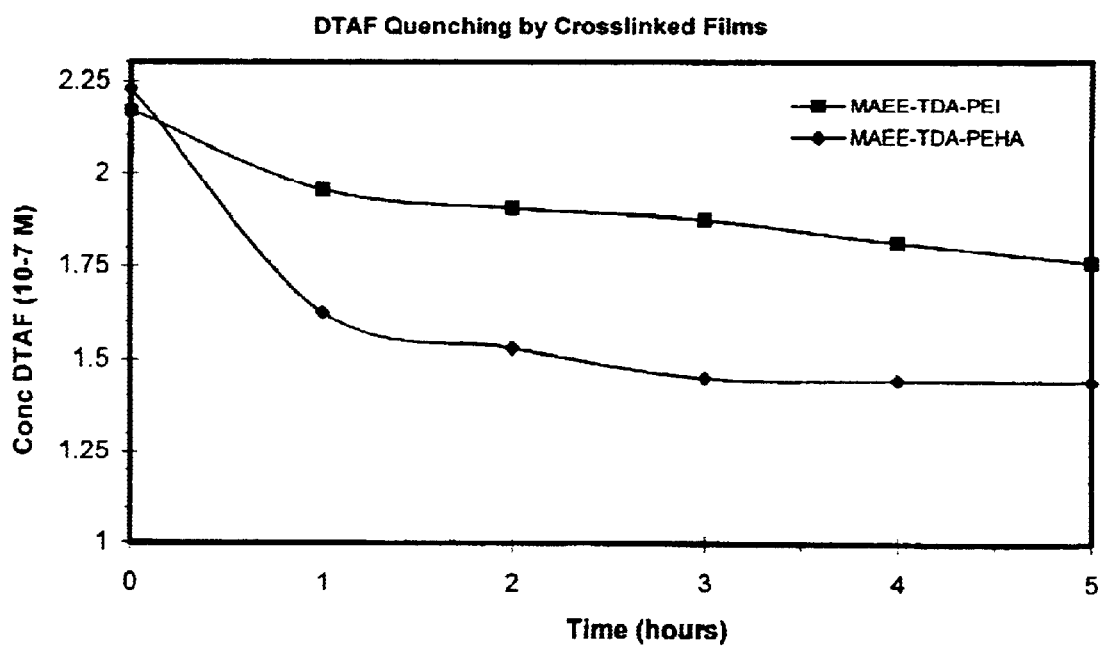
FIG. 5 is a graph illustrating quenching of DTAF by cross-linked polymer films.

A film was made from a solution of the polyamide with side chains prepared in Example 1a and the polymer prepared in Example 7a. A film was also made from a solution of the polyamide with side chains prepared in Example 1b and the polymer prepared in Example 7b. These films were placed in 5 milliliters of DTAF solution in jars covered with aluminum foil to prevent photo-bleaching. In water, the films dissolve within a few hours. This leads to a quick release of nitric oxide as shown by FIGS. 4 and 5. (Nitric oxide quenches DTAF emission.)

In order to provide optimal performance, the rate of release must be slowed so that nitric oxide will be emitted over a period of days. The polymer material must be kept on the substrate, so that water can slowly diffuse into the material, releasing nitric oxide at a controlled rate. Crosslinking the material will frequently make it less water soluble and keep the material on the substrate.

The crosslinked coatings of Example 8 used glutaraldehyde, and tris(hydroxymethyl)phosphine as crosslinking agents. A large quenching of DTAF was observed as a result of the hydroxy groups formed from crosslinking glutaraldehyde and the hydroxy groups present in tris(hydroxymethyl)phosphine magnified by an inadequate cure.

Other crosslinking agents such as diisocyanates, diethoxysilanes, titanium isopropoxide, dianhydrides were utilized. All except the diethoxysilanes quenched DTAF emissions. A film formed from the polymer of Example 1a and the polymer of Example 7a crosslinked with diethoxymethylsilane completely dissolves in water after several hours. A film formed from the polymer of Example 1b and the polymer of Example 7b crosslinked with diethoxymethylsilane does not completely dissolve. However, this coating turns the solution yellow as a result of some of the polymer leaching out. These films exhibited no additional quenching at 24 hours, and a sudden drop in emission attributed to the film dissolving in water.

Since small quantities of siloxanes do not quench DTAF emissions, other silanes were tried as crosslinking agents to see if they both hold the film on the substrate and do not quench the DTAF. Both diethoxymethyloctadecylsilane and triethoxysilane were used as crosslinking agents. However, when sufficient quantities were used to keep the film on the substrate, unreacted alkoxy groups remained to quench the DTAF. The IR of these materials shows very little Si—O stretch indicating that the cross-linking agent is attached to the polymer rather than crosslinking with itself.

Tri and tetrafunctional silanes such as triethoxysilane, triethoxymethylsilane, and tris(3-trimethoxysilyl)propyl) isocyanurate and tetraorthosilicate were combined with the polymer of Example 1a and a small quantity of water to attempt to intentionally form crosslinked nets of siloxane around the polymer. A combination using 1 gram of methyltriethoxysilane, 0.054 milliliters of water and 1 gram of the polymer of Example 1a resulted in a film that was intact days after immersion in water with no yellow color and no quenching of DTAF.

Therefore, it can be seen that the invention provides a process that efficiently prepares a polymer having side chains with a functional group that readily bonds to a nitric oxide generating functional group such that an antithrombogenic polymer may be prepared from the polymer and a compound that reacts to form nitric oxide generating functional groups on the polymer. There has also been provided a process that efficiently prepares a polymer having side chains such that an antithrombogenic polymer may be prepared from the polymer, a crosslinking agent and a compound having nitric oxide generating functional groups that is contained within the crosslinked polymer structure. The polymeric composition may be easily applied as a coating to a substrate to provide an article which has excellent antithrombogenic properties. The antithrombogenic polymeric composition has several coating applications including, without limitation, medical devices.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A polymeric composition capable of generating nitric oxide, the polymeric composition comprising: a crosslinked chemical combination of (i) a polymer having side chains along a backbone forming the polymer, at least two of the side chains containing an amino group, and (ii) a crosslinking agent containing at least two functional groups capable of reacting with the amino groups; and a plurality of nitric oxide generating functional groups associated with the crosslinked chemical combination;

wherein the polymer is a polyamide, and the polyamide is synthesized by (i) reacting a monomer selected from the group consisting of unsaturated carboxylic acids, esters of unsaturated carboxylic acids, anhydrides of unsaturated carboxylic acids, and mixtures thereof, and a first amine to form an intermediate reaction product, wherein the first amine is selected from $RR_1NH$, $RNH_2$, polyalkylene polyamines, and mixtures thereof, wherein the R and $R_1$ groups are the same or different and each contain between 1 and 50 carbon atoms and are optionally substituted with heteroatoms oxygen, nitrogen, sulfur, and phosphorus and combinations thereof, and (ii) reacting the intermediate reaction product and a second amine to form the polyamide, wherein the second amine is selected from $R_2R_3NH$, $R_2NH_2$, polyalkylene polyamines, and mixtures thereof, wherein the $R_2$ and $R_3$ groups are the same or different and each contain between 1 and 50 carbon atoms and are optionally substituted with heteroatoms oxygen, nitrogen, sulfur, and phosphorus and combinations thereof; and at least one of the selected amines includes at least two amino groups.

2. The composition of claim 1 wherein the nitric oxide generating functional groups comprise nitrate groups.

3. The composition of claim 2 wherein the nitrate groups are provided by nitrocellulose imbedded within the crosslinked chemical combination.

4. The composition of claim 1 wherein the nitric oxide generating functional groups comprise $N_2O_2^-$ groups covalently bonded to a plurality of the amino groups.

5. The composition of claim 1 wherein R and $R_1$ are alkyl and the second amine comprises a polyalkylene polyamine.

6. The composition of claim 1 wherein the monomer is selected from the group consisting of unsaturated dicarboxylic acids, esters of unsaturated dicarboxylic acids, anhydrides of unsaturated dicarboxylic acids, and mixtures thereof.

7. The composition of claim 1 wherein the monomer is selected from the group consisting of maleic anhydride, maleic acid esters, and mixtures thereof.

8. The composition of claim 7 wherein the nitric oxide generating functional groups comprise nitrate groups.

9. The composition of claim 7 wherein the nitric oxide generating functional groups comprise $N_2O_2^-$ groups covalently bonded to a plurality of the amino groups.

10. The composition of claim 8 wherein the nitrate groups are provided by nitrocellulose imbedded within the crosslinked chemical combination.

11. The composition of claim 1 wherein the crosslinking agent is selected from the group consisting of aliphatic aldehyde compounds having 2 or more —CHO groups, aromatic aldehyde compounds having 2 or more —CHO groups, and mixtures thereof.

12. The composition of claim 1 wherein the crosslinking agent is selected from the group consisting of silanes having 2 or more alkoxy groups, and mixtures thereof.

13. The composition of claim 1 wherein the crosslinking agent is selected from the group consisting of phosphines having the formula $(A)_3P$, wherein A is hydroxyalkyl, and mixtures thereof.

14. The composition of claim 13 wherein the crosslinking agent comprises tris(hydroxymethyl)phosphine.

15. A crosslinked polymeric material formed from:
(A) a polyamide formed from a mixture which comprises:
  (i) one or more monomers selected from the group consisting of unsaturated carboxylic acids, esters of unsaturated carboxylic acids, anhydrides of unsaturated carboxylic acids, and mixtures thereof; and
  (ii) one or more amines selected from the group consisting of R—$NH_2$, $RR_1NH$, polyalkylene polyamines, and mixtures thereof, wherein the R and $R_1$ groups are the same or different and each contain between 1 and 50 carbon atoms and are optionally substituted with one or more heteroatoms oxygen, nitrogen, sulfur, phosphorus, or combinations thereof; and at least one of the selected amines includes at least two amino groups;
(B) one or more crosslinking agents selected from the group consisting of silanes having 2 or more alkoxy groups; aliphatic isocyanate compounds having 2 or more —N=C=O groups; aromatic isocyanate compounds having 2 or more —N=C=O groups; aliphatic aldehyde compounds having 2 or more —CHO groups; aromatic aldehyde compounds having 2 or more —CHO groups; phosphines having the formula $(A)_2P(B)$ wherein A is hydroxyalkyl, and B is hydroxyalkyl, alkyl, or aryl; epoxy resins having end groups of the formula:

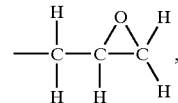

and mixtures thereof; and
(C) a plurality of nitric oxide generating functional groups associated with the crosslinked polymeric material.

16. The composition of claim 15 wherein the nitric oxide generating functional groups comprise nitrate groups.

17. The composition of claim 16 wherein the nitrate groups are provided by nitrocellulose imbedded within the crosslinked chemical combination.

18. The composition of claim 15 wherein the nitric oxide generating functional groups comprise $N_2O_2^-$ groups covalently bonded to a plurality of the amino groups.

19. The composition of claim 15 wherein the selected amine comprises tetradecylamine, pentaethylene hexamine, or a mixture thereof.

20. The composition of claim 15 wherein the monomer is selected from the group consisting of unsaturated dicarboxylic acids, esters of unsaturated dicarboxylic acids, anhydrides of unsaturated dicarboxylic acids, and mixtures thereof.

21. The composition of claim 15 wherein the monomer is selected from maleic anhydride, maleic acid esters, and mixtures thereof.

22. The composition of claim 21 wherein the nitric oxide generating functional groups comprise nitrate groups.

23. The composition of claim 21 wherein the nitric oxide generating functional groups comprise $N_2O_2^-$ groups covalently bonded to a plurality of the amino groups.

24. The composition of claim 22 wherein the selected amine comprises at least one alkyl amine and at least one polyalkylene polyamine.

25. The composition of claim 15 wherein the crosslinking agent is selected from the group consisting of aliphatic aldehyde compounds having 2 or more —CHO groups, aromatic aldehyde compounds having 2 or more —CHO groups, and mixtures thereof.

26. The composition of claim 15 wherein the crosslinking agent is selected from the group consisting of silanes having 2 or more alkoxy groups, and mixtures thereof.

27. The composition of claim 15 wherein the crosslinking agent is selected from the group consisting of phosphines having the formula $(A)_2P(B)$, wherein A and B are hydroxyalkyl, and mixtures thereof.

28. The composition of claim 27 wherein the crosslinking agent comprises tris(hydroxymethyl)phosphine.

29. The composition of claim 15 wherein,
the monomer comprises at least one of maleic anhydride, maleic acid ester or a mixture thereof;
the selected amine comprises at least one alkyl amine and at least one polyalkylene polyamine; and
the selected crosslinking agent comprises an aliphatic dialdehyde and at least one phosphine having the formula $(A)_2P(B)$, wherein A and B are hydroxyalkyl.

30. A crosslinked polymeric material formed from:
(A) a polyamide formed from a mixture which comprises:
  (i) one or more monomers selected from the group consisting of maleic anhydride, maleic acid esters, and mixtures thereof; and
  (ii) one or more amines selected from the group consisting of R—$NH_2$, $RR_1NH$, polyalkylene polyamines, and mixtures thereof, wherein the R and R$_1$ groups are the same or different and each contain between 1 and 50 carbon atoms and are optionally substituted with heteroatoms oxygen, nitrogen, sulfur, phosphorus, or combinations thereof; and at least one of the selected amines includes at least two amino groups;

(B) one or more crosslinking agents selected from the group consisting of aliphatic isocyanate compounds having 2 or more —N=C=O groups; aromatic isocyanate compounds having 2 or more —N=C=O groups; silanes having 2 or more alkoxy groups; aliphatic aldehyde compounds having 2 or more —CHO groups; aromatic aldehyde compounds having 2 or more —CHO groups; phosphines having the formula (A)$_2$P(B) wherein A is hydroxyalkyl, and B is hydroxyalkyl, alkyl, or aryl; epoxy resins having end groups of the formula:

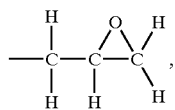

and mixtures thereof; and (C) a plurality of nitric oxide generating functional groups associated with the crosslinked polymeric material.

31. The composition of claim 30 wherein the nitric oxide generating functional groups comprise nitrate groups.

32. The composition of claim 31 wherein the nitrate groups are provided by nitrocellulose imbedded within the crosslinked polymeric material.

33. The composition of claim 30 wherein the nitric oxide generating functional groups comprise N$_2$O$_2^-$ groups covalently bonded to a plurality of the amino groups.

34. The composition of claim 30 wherein the selected amine comprises at least one polyalkylene polyamine.

35. The composition of claim 34 wherein the selected amine comprises tetradecylamine, pentaethylene hexamine, or a mixture thereof.

36. The composition of claim 30 wherein the crosslinking agent is selected from the group consisting of aliphatic aldehyde compounds having 2 or more —CHO groups, aromatic aldehyde compounds having 2 or more —CHO groups, and mixtures thereof.

37. The composition of claim 30 wherein the crosslinking agent is selected from the group consisting of silanes having 2 or more alkoxy groups, and mixtures thereof.

38. The composition of claim 30 wherein the crosslinking agent is selected from the group consisting of phosphines having the formula (A)$_2$P(B), wherein A and B are hydroxyalkyl, and mixtures thereof.

39. The composition of claim 38 wherein the crosslinking agent comprises tris(hydroxymethyl)phosphine.

40. A crosslinked polymeric material formed from:

(A) a polyamide formed from a mixture which comprises:
   (i) one or more monomers selected from the group consisting of maleic anhydride, maleic acid esters, and mixtures thereof; and
   (ii) one or more amines selected from the group consisting of R—NH$_2$, RR$_1$NH, polyalkylene polyamines, and mixtures thereof; wherein the R and R$_1$ groups are the same or different and each contain between 1 and 50 carbon atoms and are optionally substituted with heteroatoms oxygen, nitrogen, sulfur, phosphorus, or combinations thereof; and at least one of the selected amines includes at least two amino groups;

(B) one or more crosslinking agents:

(C) a plurality of nitric oxide generating functional groups associated with the crosslinked polymeric material.

* * * * *